(12) United States Patent
Kambhatla et al.

(10) Patent No.: US 6,238,337 B1
(45) Date of Patent: May 29, 2001

(54) MEDICAL NON-INTRUSIVE PREVENTION BASED ON NETWORK OF EMBEDDED SYSTEMS

(75) Inventors: Nanda Kambhatla, Elmsford; Dimitri Kanevsky, Ossining; Wlodek W. Zadrozny, Tarrytown; Alexander Zlatsin, Yorktown Heights, all of NY (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 09/350,626

(22) Filed: Jul. 9, 1999

(51) Int. Cl.$^7$ ........................................... A61B 5/00
(52) U.S. Cl. ............................. 600/300; 705/3
(58) Field of Search ................... 600/300–301, 600/481, 500, 529, 538, 544–545; 128/900–905, 920, 925; 705/1–3; 700/241, 213–215

(56) References Cited

U.S. PATENT DOCUMENTS

| | | | |
|---|---|---|---|
| 5,619,991 | * 4/1997 | Sloane | 600/300 |
| 5,911,132 | * 6/1999 | Sloane | 600/300 |
| 5,938,594 | * 8/1999 | Poon et al. | 600/300 |
| 6,032,084 | * 2/2000 | Anderson et al. | 700/241 |

\* cited by examiner

Primary Examiner—Eric F. Winakur
Assistant Examiner—Michael Astorino
(74) Attorney, Agent, or Firm—Scully, Scott, Murphy & Presser; Daniel P. Morris, Esq.

(57) ABSTRACT

The invention detects signs of emerging illness, such as flu, skin cancer, backache, etc., among the general population and individuals. The detection of symptoms of illness is performed through the utilization of embedded devices equipped with various sensors, such as cameras, glasses, wrist watches, TVs, fire warning systems, and having the ability to analyze the detected information and to transmit that information via wireless and regular communication channels to a central server for a more detailed analysis and possible action. The information about locally detected symptoms is gathered at central location and processed to ascertain whether there is a new epidemic of a flu, therefore enabling early shipment of a flu vaccine which prevents the spread of the disease.

39 Claims, 7 Drawing Sheets

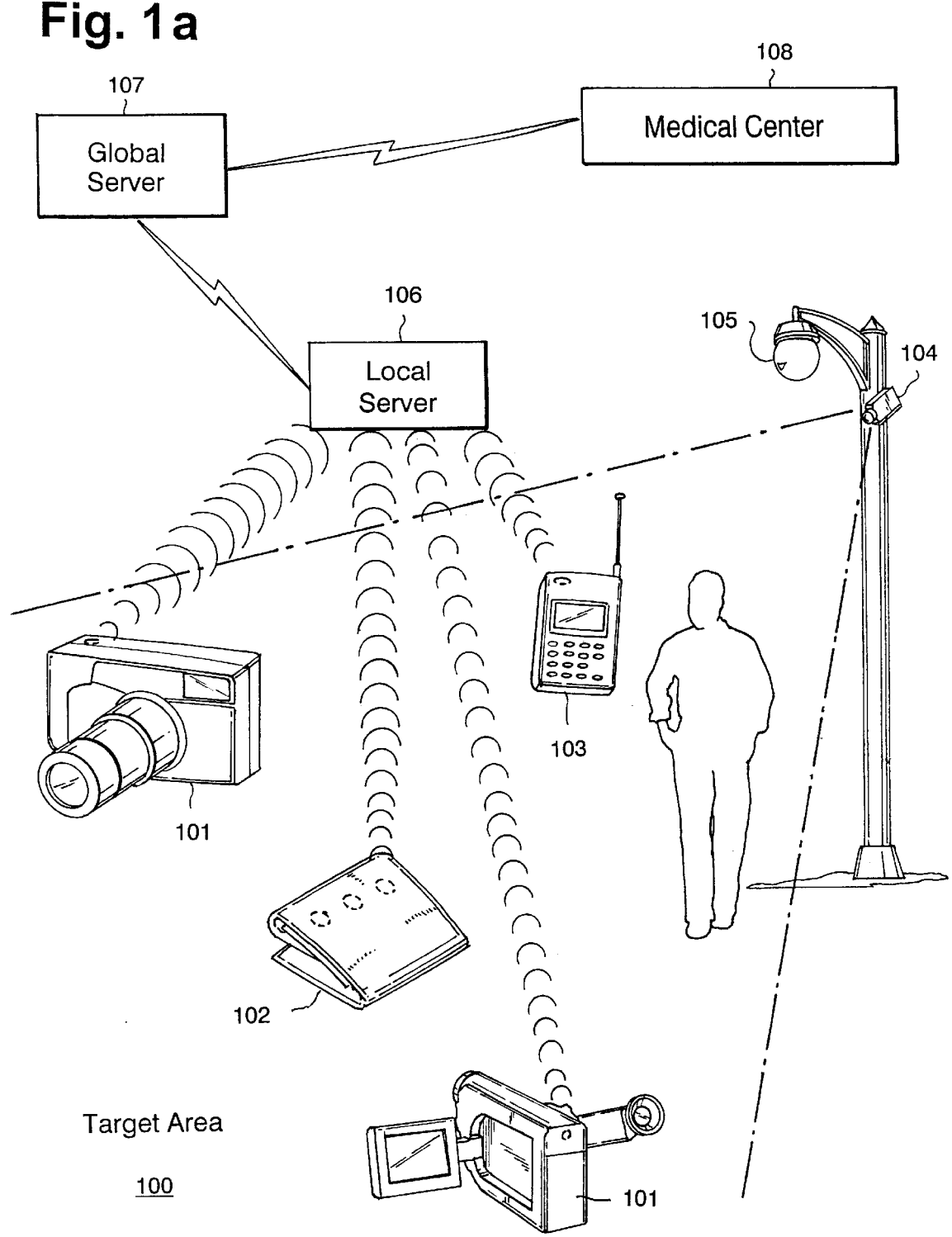

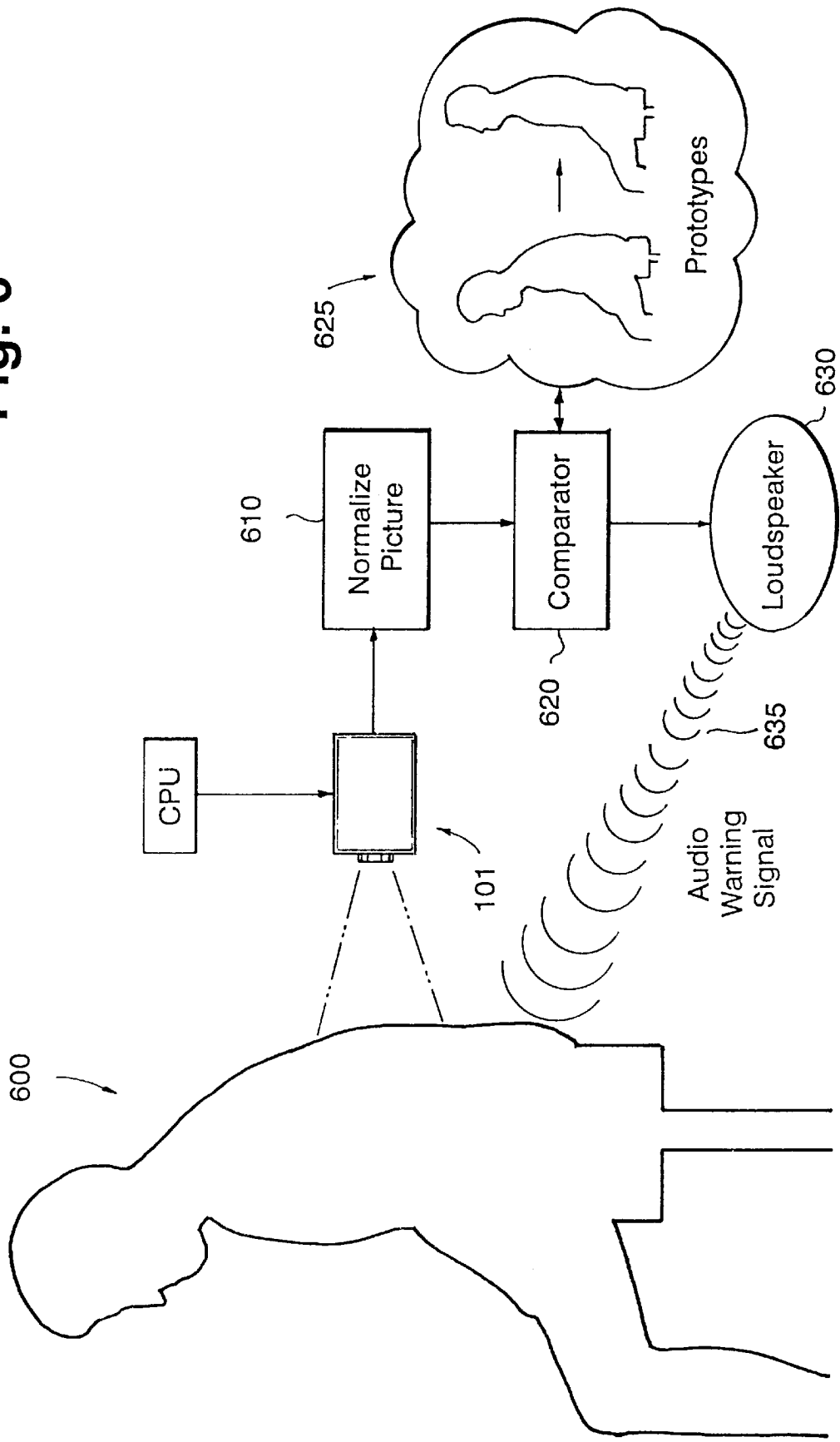

MEDICAL NON-INTRUSIVE PREVENTION BASED ON NETWORK OF EMBEDDED SYSTEMS

BACKGROUND OF THE INVENTION

1. Field of the Invention

The invention relates to the detection and reporting of symptoms of illness in individuals and in a general population and more particularly to using a network of embedded devices equipped with sensors for detection and analysis of symptoms of illness.

2. Description of Prior Art

Presently illness detection occurs relatively late, usually when a large segment of the population is already affected by the illness and visits to doctors' offices and hospitals become necessary to relieve the symptoms. Sometimes, because of the number of infections, such visits to the medical professionals may come close to overwhelming the local health systems. Furthermore, because of this lateness of detection, not enough time can be allocated for preparation and distribution of preventive vaccine among the general population, or for formulation and distribution of a new vaccine where a new type of illness, such as flu, is developed.

Early detection may also provide much better chances of successful treatment of diseases such as skin cancer. Today, detection of diseases such as skin cancer, typically occurs during visits to the doctor's office. However, at best, such visits occur once a year. Furthermore, the educated examination of the skin condition even once a year is not satisfactory for early detection of the cancer symptoms.

Another common malady afflicting the general population is the backache problem. The backache problems are usually caused by such factors as the sitting posture. Ever increasing numbers of workers spend their work days in chairs behind desks and in front of computer screens, most do not use proper sitting posture thereby developing back problems. If the posture and back problems are not detected early, the treatment of those problems will become increasingly more difficult and expensive.

What is needed is a way to prevent the spread of various illnesses like the flu, some forms of cancer, backache, etc., through early detection. For example, early detection of flu symptoms in the general population will lead to the early distribution of the flu vaccine among the population with weak immune systems, such as children and senior citizens, thereby protecting the population at large.

SUMMARY OF THE INVENTION

The object of the present invention is the detection and the reporting of illness symptoms in the general population for the purpose of prevention. The invention utilizes embedded devices equipped with sensors and having an ability to analyze captured data thereby detecting the emergence of illness, such as the flu, skin cancer, backache etc., among individuals and the general populations. The embedded devices may be equipped with communication interface ports for transmitting the captured data from the embedded devices to the local servers for data processing. The local servers may be further connected to the global servers and to the medical centers and individuals by a network which may be comprised of Internet, Intranet, LAN, infrared and wireless communication channels and any variety of a communications network allowing the interconnection of computing devices and the passage of the information.

The employed embedded devices transmitting the data may be installed in the commonly used appliances, such as digital video cameras, eyeglasses, wrist watches, television sets, fire warning systems etc. Those devices may be programmed to detect the common flu symptoms such as sneezing, coughing and nose blowing. The information and images of locally detected symptoms may be gathered at the central servers and processed to ascertain whether a new flu outbreak is at hand. If such an outbreak is diagnosed, the information may be used to advocate for distribution of a vaccine to the targeted segments of the population.

The photo and video cameras equipped with special sensors and embedded processors, specifically cameras used by tourists may be especially useful in the detection of certain types of illnesses. Those cameras may detect new contagion causing viruses and bacteria brought in from abroad. Conversely, these same cameras may detect enough symptoms of illness among the local population to enable the inventive system to the local officials.

Another example of the placement of the embedded devices may be a target individual's bathroom. A camera with an embedded device having a processor programmed to take daily images of the target individual's skin regions while the target individual is habitually following a toilet routine. The daily images of same skin regions are then compared to detect changes signaling skin cancer concerns. Furthermore, this locally embedded cancer detection system may pass gathered information to a central server for a more complex analysis of detected symptoms and for the purpose of collection of statistical data. The central server may have the ability to collect statistical data from many reporting locations thereby having an ability to associate cases of disease with possible regional and global environmental factors.

Another wide spread illness which may be detected and reported by the invention is the backache. The development of the backache problem may be prevented by installing embedded sensors near the sitting areas in offices and at home. These embedded sensors may send images to the embedded systems capable of analyzing whether the target's sitting posture will cause back problems. Again, similar to the discussion above, these embedded systems may be connected to local servers for performing more complicated analysis.

When the first signs of bad sitting posture are detected, a warning signal, to correct the sitting position, may be given, i.e., via a speaker or e-mail. Such a monitoring system may be especially useful for monitoring the children's posture while they are doing their homework, reading or watching television. The warning signal may be sent not only to the children but also to their parents or guardians. Similarly, other problems such as keeping the proper eye distance from a book while the children are reading, properly brushing their teeth, etc., may be addressed by the present invention.

BRIEF DESCRIPTION OF DRAWINGS

The foregoing objects and advantages of the present invention may be more readily understood by one skilled in the art with reference being had to the following detailed description of a preferred embodiment thereof, taken in conjunction with the accompanying drawings wherein like elements are designated by identical reference numerals throughout the several views, and in which:

FIG. 1a is a pictorial diagram of a distributed network of embedded devices having sensors for detecting and reporting the signs of virus epidemics and other illnesses;

FIG. 6 is a diagram of the inventive system used in detection of backache.

DETAILED DESCRIPTION OF THE INVENTION

Figure 1B:
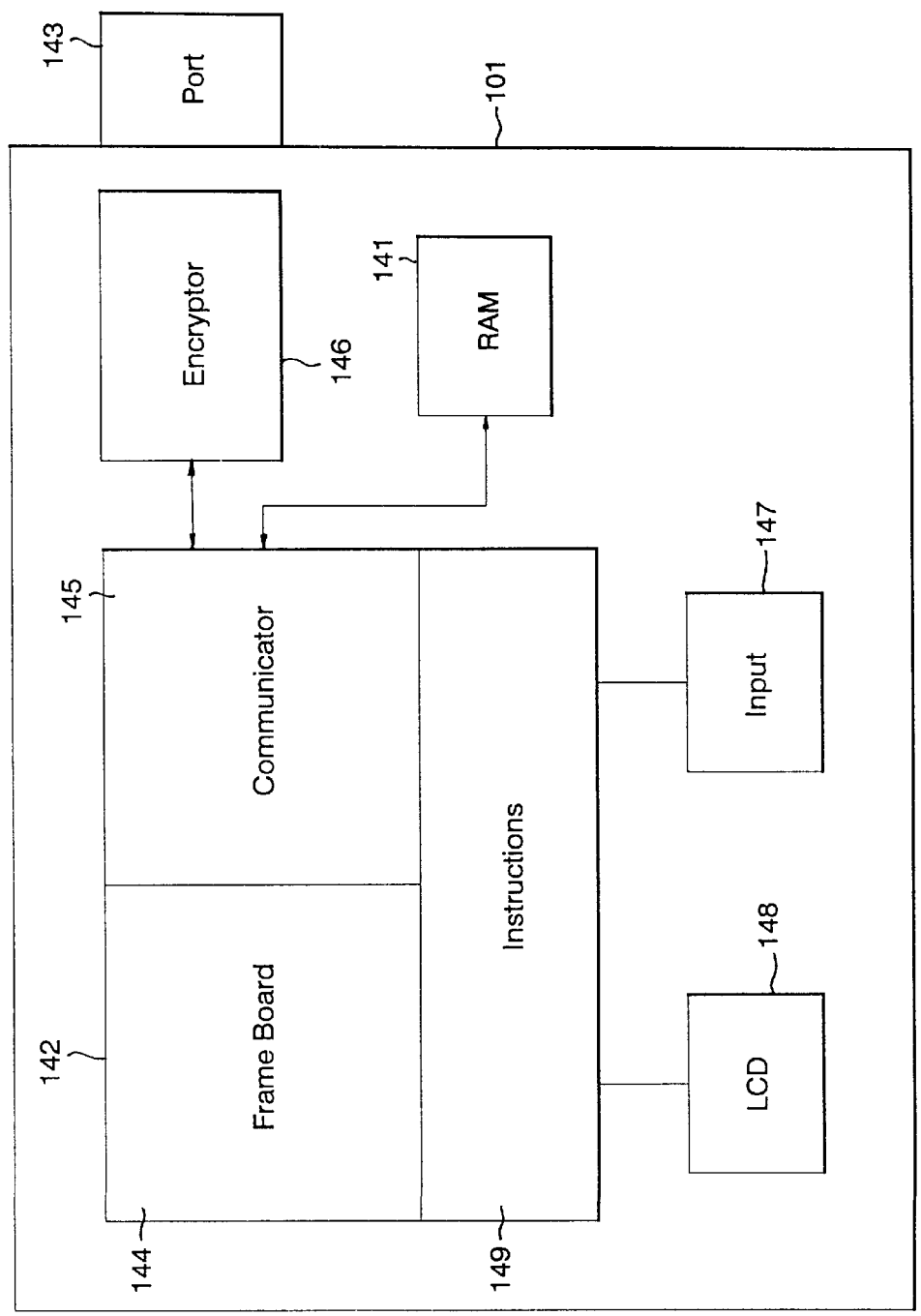
FIG. 1b is a diagram of a camera with a video sensor used in conjunction with the present invention.

Shown in FIG. 1a is a distributed network of embedded devices with sensors to provide visual information about the environment surrounding the embedded device in order to detect and report signs of viruses, epidemics, and other illnesses. The embedded devices may be distributed among the people in the target area 100, or be fixed on landmarks such as a street post or a street light 105 having a security camera 104. The audio sensors of the invention, i.e., a microphone, may be part of devices such as computers, palmtops, tape recorders, telephones 103, cameras 101, and other types of recording apparatus.

The video sensors of the invention, may be part of devices such as all types of light detecting equipment including video, photo, television and closed caption cameras 101. The partial detail of such cameras 101 is shown in FIG. 1b. The camera 101 contains the flash memory (RAM) 141 for storing pictures, a board 142 and a port 143 for communicating pictures through media such as wireless channels. The board 142 may contain two components, a frame board 144 for the production of frames from the captured images, storing those images in RAM 141 and a communicator 145 for selecting and sending frames from RAM 141 to the communications port 143. Additionally, a data encryptor 146, input port 147, and a light crystal display 148, as well as a processor for instruction execution 149, may be included as part of the camera 101.

Returning now to FIG. 1a, pulse rate, body temperature, and blood pressure sensors may be provided as part of devices such as watches or rings or wallets 102 to be worn by individuals being monitored. Additionally, motion detection sensors, to detect presence of potential monitoring subject in the vicinity of the embedded device, may also be utilized to initiate automatic collection of information.

Data captured by sensors, e.g., images and sounds, may be stored in embedded devices' memories and downloaded via wireless connections to the local servers 106. Data may further be sent, via the network, to storage located on the global servers 107, where data may be analyzed by special programs to detect specific symptoms typical of illnesses being monitored, for example a fever, a cold, and coughs and sneezes for flu.

The method of data downloading and transmission of data from the embedded devices to local servers is described in a commonly owned, co-pending U.S. patent application Ser. No. 09/225,800 filed on Jan. 5, 1999 and entitled "Non Intrusive Automatic Remote Support For Freeing Overloaded Storage in Portable Devices" the contents of which are incorporated herein by reference. If the analysis of data determines that there is a large number of people having flu-like symptoms, the information may be forwarded to a medical center 108, where appropriate actions, such as the virus identification and the making of a vaccine may be undertaken.

Figure 2:
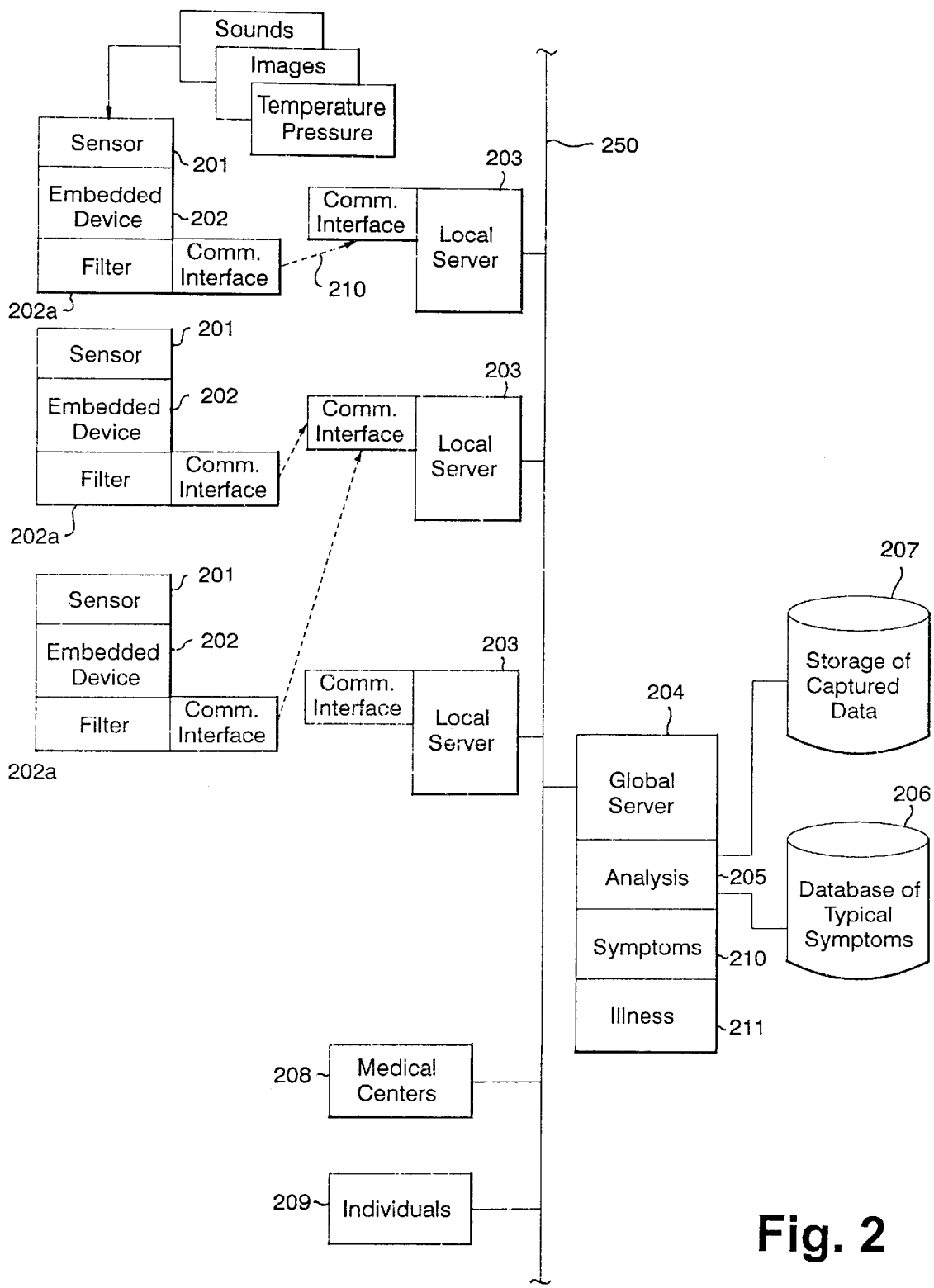
FIG. 2 is a block diagram of the top level of the network of embedded devices, servers, databases, and the warning system for monitoring single and numerous individuals for detection of medical symptoms.

FIG. 2 shows a block diagram of a network system of embedded devices, servers, databases, and warning receivers, for detecting and reporting medical symptoms to monitor single and multiple individuals. The embedded devices 202 may contain a filter module 202a for reducing the amount of data to be transmitted for storage and processing on the local servers 203. Embedded devices 202 may also have an ability to count the number of individuals in each collected sample of data. The embedded devices may be equipped with a communications interface 210 and with sensors 201 positioned at different locations to receive sound, visual information, and other information, such as the body temperature and blood pressure 200 from surrounding environment and people.

Typically, a wireless connection is used to download data collected by the embedded devices to local servers 203. Local servers 203 may be installed in various buildings and landmarks in locations where embedded devices commonly appear. The collected data is forwarded by the local servers 203, via the network 250, to the global servers 204 where it is stored in the storage 207. The local servers 203 are capable of analyzing data, provided by embedded devices 202, and to determine whether any changes are taking place from one day to the next. For example, embedded devices with audio sensors installed in a movie theater may record the number of sneezes during a two hour viewing session. The local server may then determine if the number of sneezes is on the increase, by comparing the data downloaded on two consecutive days. The number of patrons may be ascertained from the ticket sales.

If the local server decides that it detected the onset of illness, i.e., the number of sneezes during comparable time period in comparable size audience has increased, then the global server 204, through the use of the module 205, evaluates wether the local server 203 has in fact detected the onset of illnesses in individuals and epidemics in populations at large. The module 205 performs analysis of data by querying a database of typical images, sounds, and gestures 206 related to symptoms 210 of a possible illness and comparing them to the most recent data. For example, flu symptoms may include sneezing, coughing and blowing one's nose and skin cancer symptoms include the appearance of moles and skin lesions. Additional information from various sources, such as statistical data provided by the center for disease control, regional hospital statistics, and sales data of certain over the counter and prescription medication may be provided to augment the symptom database 206.

Methods for archiving, indexing, classifying, and retrieving of data of different types, such as images, sounds, and gestures, and the comparison of the archived data with individual data items are described in a commonly owned, co-pending U.S. patent application Ser. No. 09/063,805 entitled "Random Visual Patterns Used to Obtain Secured Access" filed on Apr. 21, 1998 and in a commonly owned, co-pending U.S. patent application Ser. No. 09/079,754 entitled "Apparatus and Methods for User Recognition Employing Behavioral Passwords" filed on May 15, 1998.

Individual data items collected at different times and time stamped accordingly, may also be compared among themselves to detect gradual changes in some patterns that may lead to detection of some illnesses like skin cancer characterizes by special changes in certain skin patterns.

Medical centers 208 and individuals 209 may be connected to the global servers 204 to obtain warning signals and information about detected symptoms, such as when, where, and how often they were detected. These warning signals and data may be sent to global servers 204 by the analysis module 205 if certain criteria are met. The criteria may include the following:

1. the observed matches of a sequence of individual data items in storage 207 and prototypes in database 206 indexed by possible symptoms 210 of illnesses 211; and
2. a number of matches between observed sequences of individual items and stored prototypes exceeds a certain threshold.

The global servers 204 may forward this information to appropriate medical centers 208, which may in turn proceed to obtain information and perform certain actions including contacting special, appropriate organizations and individuals, depending on the information received. For example, if the information received included symptoms pointing to the beginning of flu onset, then medical centers 208 may contact laboratories or factories producing flu vaccine in order to speed up the start of a vaccines' production. The medical centers 208 may also send warnings and notifications to people in the position to benefit from such flu vaccine.

In another example, the medical centers 208 may receive information from beaches about increased number of people having skin-cancer symptoms. Here, the medical centers may take actions such as public announcements directed to decreasing the sun exposure of prospective beach goers through the use of sun-protecting creams, and staying in doors and in shadows. The medical centers 208 may also send warning data to environmental centers if a determination is made that the increased cancer symptoms are associated with the ozone depletion or some other environmental problems.

If medical centers 208 receive information about specific individuals 209, through embedded sensors of the inventive system located at individuals' home, then medical centers 208 will forward special warnings, such as requests to visit a doctor for an examination and to possibly receive a vaccine inoculation. The medical centers 208 may also send request for additional information about specific symptoms and receive the requested data from the global servers 204 when data is obtained from the analysis module 205.

Individual symptoms 209 may include the appearance of tumors, colds, fever, diarrhea, indigestion, food poisoning, symptoms pointing to asthma, anemia, diabetes, shortness of breath, flu, cancer etc. The analysis module 205 and the global servers 204 may further determine what information, and when it should be sent to which medical centers 208 and to which individuals 209.

Figure 3:
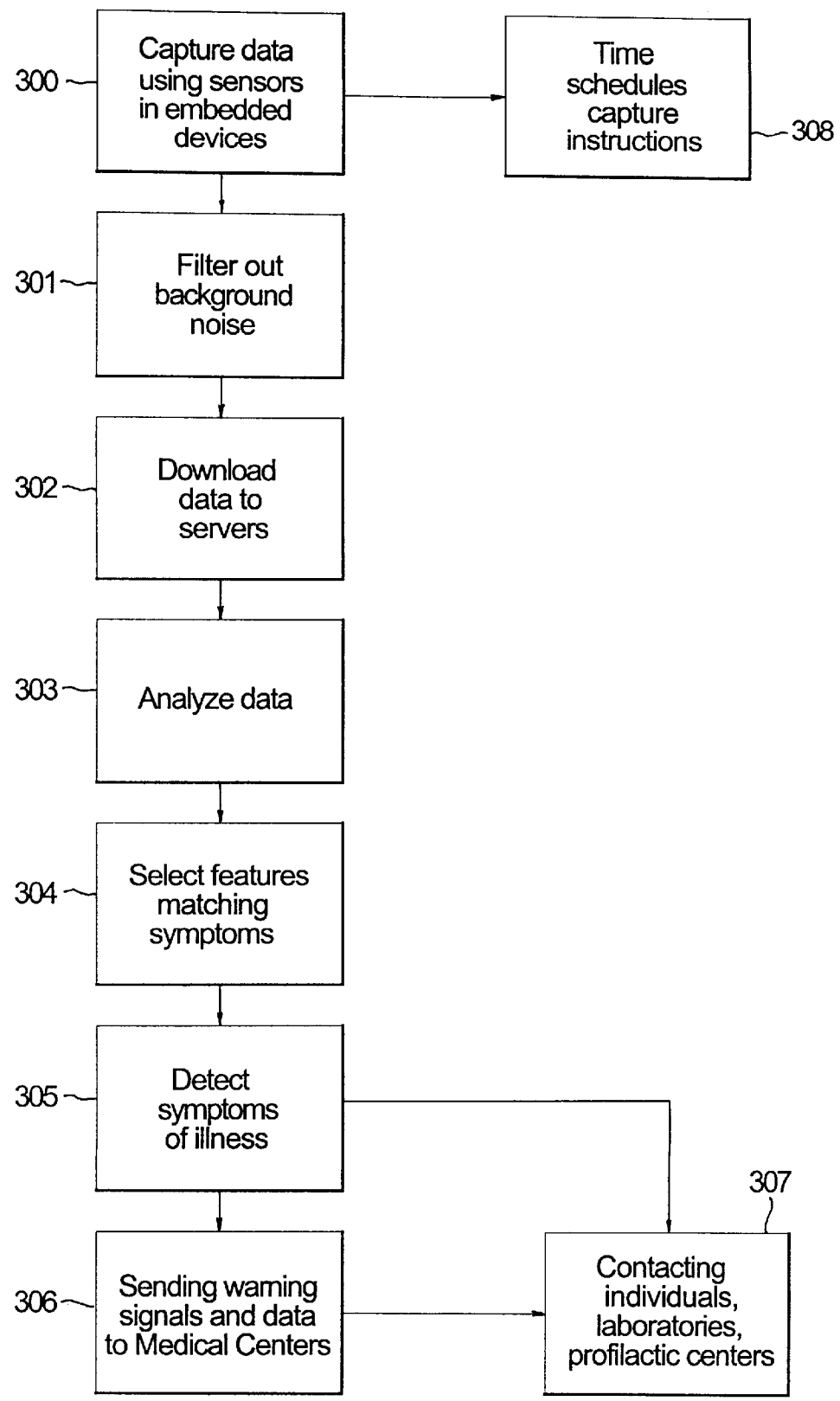
FIG. 3 is a flow diagram for processing data by the inventive network of devices described in FIG. 2.

FIG. 3 shows the basic processing flow of the invention. The capturing of data by the embedded devices' sensors, may be performed automatically according to the time schedules in conjunction with preloaded instructions supplied at step 308 or manually initiated at step 300 by individuals in control of the apparatus having embedded devices containing sensors.

After being captured by sensors of the embedded devices 201 (FIG. 2) in the step 300, the data is filtered in the step 301 to reduce the amount of information to be sent for storage and processing. The filtering may eliminate irrelevant or redundant information sent over the network. This procedure allows the reduction of the amount of data transferred to the local servers 203 (FIG. 2). Because the filtering is performed by processors of the embedded devices, only relatively simple filtering tasks requiring limited CPU power may be performed. The filtering may include 1. the noise reduction,
2. the removal of the pictorial background to isolate the relevant information by detecting only moving objects, and
3. the removal of the redundant information such as repeating events.

Data is downloaded to local servers in the step 302 and analyzed, in the step 303. The analysis step 303 produces features used by the matching/selecting step 304. The stored prototype features are matched in order to select features leading to the detection of the medical symptoms in step 305. If such symptoms are detected, a warning signal system for sending this data to medical centers is activated at the step 306. The medical centers analyze the data and send warning signals and recommendations to individuals, laboratories and community centers at the step 307.

Figure 4:
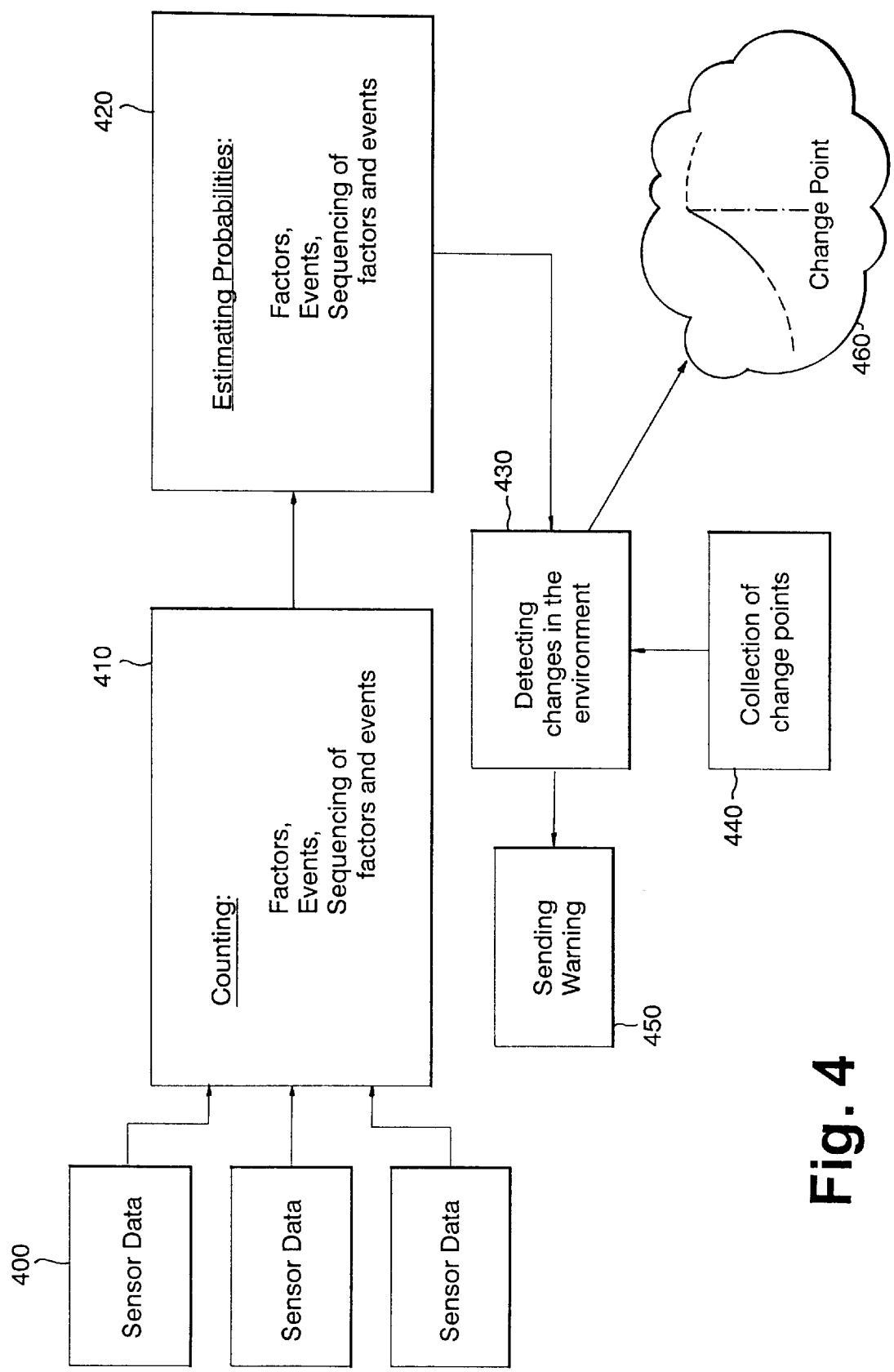
FIG. 4 is a flow diagram for performing statistical gathering and analysis of the present invention.

The present invention utilizes statistical analysis for the evaluation of the received data. As shown in FIG. 4, after data is received from the embedded devices 400, various factors, events and sequences are counted at step 410. Probabilities of those factors, events and sequences are estimated by local processes at step 420. At step 430, changes in the environment may be detected, by comparing the received data with stored factors and events provided at step 440. The provided factors and events may include behavioral patterns such as coughing, nose blowing, sneezing, sleeping, eating, time of arrival at work, i.e., being late, sitting posture, reading patterns, i.e., book holding distance, skin pigmentation patterns, moles, rushes, hair condition, body temperature, pulse readings, and others.

The invention may customize the change point of all factors and events, shown at step 460. The known change points are described in Yaschin, Emmanuel, ?Weighted Cumulative Sum technique?, Technometrics, 1989, Vol. 31, 321–338; Yaschin, Emmanuel, ?Statistical Control Schemes: Methods, Applications, and Generalization? International Statistical Review, 1992, Vol. 61, No. 1, 41–66; and Yaschin, Emmanuel, ?Likelihood Ratio Methods for Monitoring Parameters of a Nested Random Effect Model?, Journal of the American Statistical Association, June 1995, Vol. 90, No. 430, Theory and Methods, pp. 729–737. The ability to customize the change point may be used to adjust to seasonal and regional discrepancies and expectations based on historical statistical analysis. Returning to the movie theater example, in the summer the change point may be set to 30 sneezes per 100 movie patrons in two hours. In the winter, that number may be increased either outright, i.e., 40 sneezes per 100 patrons, or by a percentage, i.e., a 33% increase in sneezes. If the detected change point was reached, the dispatch of a warning becomes necessary, such warning signals and relevant information are then issued at step 450.

Figure 5:
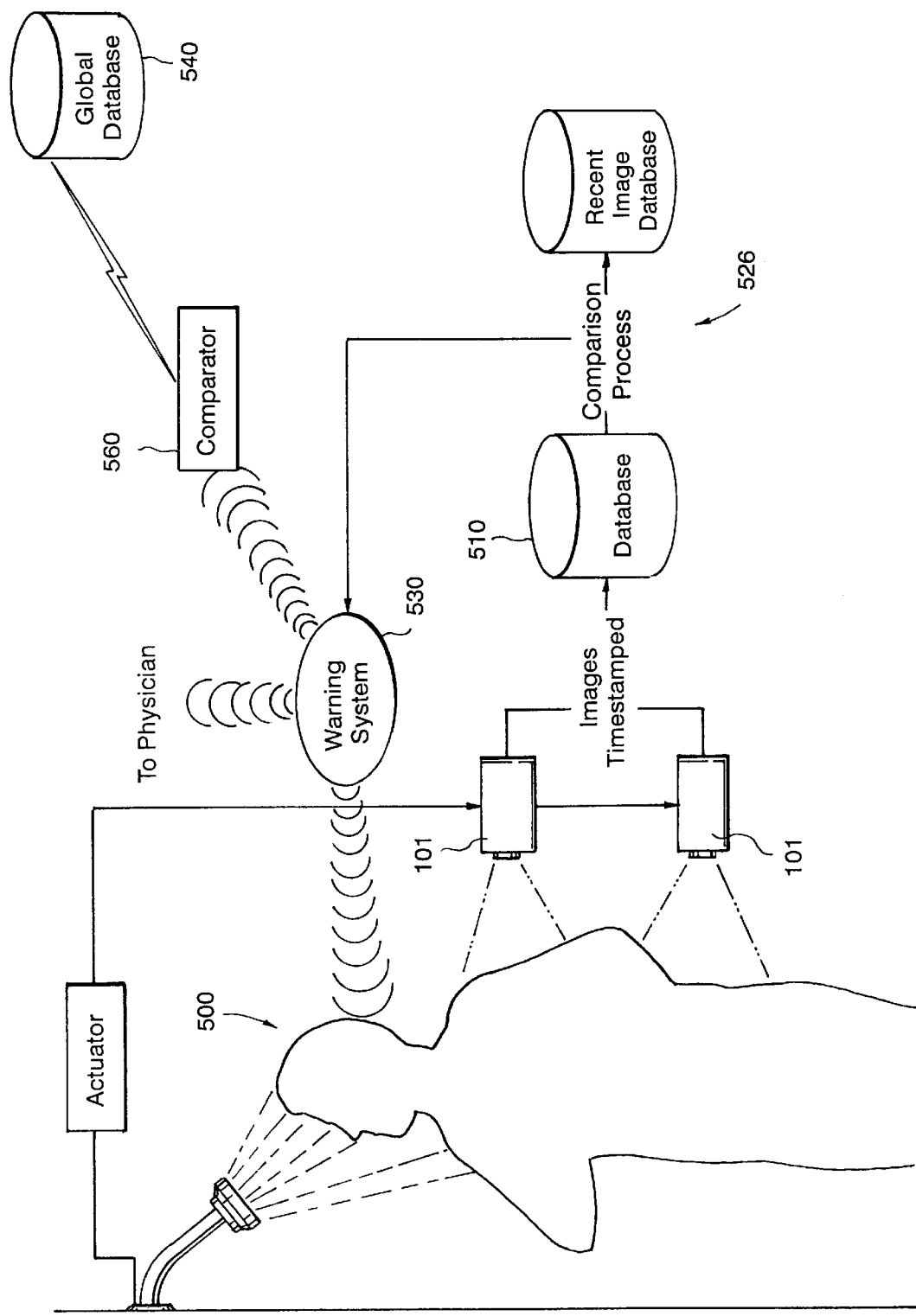
FIG. 5 is a diagram of the inventive system used in detection of the skin cancer.

In addition to detecting illnesses like flu, the inventive system may be utilized in the detection of skin cancer and back problems. Shown in FIG. 5, is an installation of the inventive system in a target individual's 500 bathroom where cameras 101 take daily images of the regions of the target individual's 500 skin. The images are time stamped, stored in a database 510, and compared to the recently stored images by process 520. If the skin deterioration is detected, a warning system 530 may warn the target individual 500, a physician, and other authorized parties, as well as forward the suspect data to a global database 540 for further comparison and for the general information gathering. The comparator 560 compares the time stamped images to the historical database of previously taken images of the skin regions of the target individual 500 and also to various stored patterns and symptoms to determine what illness or what stage of illness may be attributed to the received time stamped image.

FIG. 6 shows the target individual 600 being monitored for early detection of the back problems. A camera 101 may be taking periodic pictures of the target individual's 600 sitting posture, normalizing that image at the step 610 to make it compatible with the available prototype images 625 of possible proper and improper sitting postures, with which the image may be compared at the step 620. If the inventive system detects a problem with the target individual's 600 posture, a warning signal 635 reminding the target individual 600 to change the sitting position may be sounded over a loudspeaker 630. In another embodiment, the warning signal 635 may be sent as an e-mail message to the target individual 600 or the company's management.

While the invention has been particularly shown and described with respect to illustrative and preferred embodiments thereof, it will be understood by those skilled in the art that the foregoing and other changes in form and details may be made therein without departing from the spirit and scope of the invention that should be limited only by the scope of the appended claims.

Having thus described our invention, what we claim as new, and desire to secure by Letters Patent is:

1. A system for detecting an onset of illnesses and epidemics and preventing the illnesses and epidemics from occurring in individuals and a general population, said system comprising:
    a means for collecting information relating to health of individuals in a populated area via devices with sensors, said information being collected non-intrusively;
    a means for transferring said collected information from said devices with sensors to a computer processing means; and
    said computer processing means for comparing collected information against a first database for determining if said collected information indicates symptoms relating to said onset of illnesses, wherein diagnosis and prevention of the illnesses and epidemics in individuals is accomplished automatically without human intervention.

2. The system of claim 1, wherein said devices with sensors are positioned at various fixed locations and with individuals.

3. The system of claim 2, wherein said means for collecting information comprises a means for filtering said collected information.

4. The system of claim 3, wherein a number of people in each segment of said collected information is counted.

5. The system of claim 4, wherein said collection of information is initiated by an event selected from the group consisting of a
    receiving a signal from said processing means;
    detecting of a number of people, in a vicinity of said devices with sensors, exceeding a certain threshold; and
    detecting of a preset condition by said devices with sensors.

6. The system of claim 4, wherein said first database comprises symptoms, conditions and patterns of different illnesses.

7. The system of claim 6, wherein said symptoms include appearance of tumors, colds, fever, indigestion, food poisoning, asthma, anemia, diabetes, shortness of breath.

8. The system of claim 6, wherein said conditions include a higher than average body temperature, coughing, sneezing and nose blowing.

9. The system of claim 6, wherein said computer processing means comprising:
    a means for receiving said collected information from said devices with sensors;
    a means for saving said collected information in a historical storage of said collected information; and
    a first comparison means for comparing said collected information with information from said historical storage to determine if there is an increase of symptoms constituting an illness.

10. The system of claim 9, wherein said computer processing means further comprises a second comparison means for comparing said collected information with information from said database to determine what particular illness is represented by said increased symptoms determined by said first comparison means.

11. The system of claim 10, wherein said computer processing means further comprise a means to provide statistical analysis consisting of counting various factors, events and, sequences in said filtered information and estimating probabilities of said factors, events, and sequences.

12. The system of claim 11, wherein said various factors, events and, sequences include coughing, nose blowing, sneezing, behavioral patterns, sleep, eating, on-time arrival at work, sitting posture, reading posture, skin pigmentation patterns, moles, rushes, body temperature, and pulse rate.

13. The system of claim 11, further comprising a warning means for notifying medical centers and individuals about detected symptoms of illness and if requested, forwarding said collected information to said medical centers and individuals.

14. A method for detecting an onset of illnesses and epidemics and preventing the illnesses and epidemics from occurring in individuals and a general population, said method comprising the steps of:
    collecting information relating to health of individuals in a populated area via devices with sensors, said information being collected non-intrusively;
    communicating said collected information for processing by a computer processing means; and
    comparing collected information against a first database for determining if said collected information indicates symptoms relating to said onset of illnesses, wherein diagnosis and prevention of the illnesses and epidemics in individuals is accomplished automatically without human intervention.

15. The method of claim 14, wherein said devices with sensors are positioned at various fixed locations and with individuals.

16. The method of claim 15, wherein said collected information is filtered.

17. The method of claim 16, wherein a number of people in each segment of said collected information is counted.

18. The method of claim 17, wherein said collection of information is initiated by an event selected from the group consisting of a
    receiving a signal from said computer processing means;
    detecting of a number of people, in a vicinity of said devices with sensors, exceeding a certain threshold; and detecting of a preset condition by said devices with sensors.

19. The method of claim 17, wherein said first database comprises symptoms, conditions and patterns of different illnesses.

20. The method of claim 19, wherein said symptoms include appearance of tumors, colds, fever, indigestion, food poisoning, asthma, anemia, diabetes, shortness of breath.

21. The method of claim 19, wherein said conditions include a higher than average body temperature, coughing, sneezing and nose blowing.

22. The method of claim 19, further comprising the steps of:

receiving said collected information from said devices with sensors;

saving said collected information in a historical storage of said collected information; and comparing said collected information with information from said historical storage to determine if there is an increase of symptoms constituting an illness.

23. The method of claim 22, further comprising a step of comparing said collected information with information from said database to determine what particular illness is represented by said increased symptoms determined by said first comparison means.

24. The method of claim 23, further providing statistical analysis consisting of counting various factors, events and, sequences in said filtered information and estimating probabilities of said factors, events, and sequences.

25. The method of claim 24, wherein said various factors, events-and, sequences include coughing, nose blowing, sneezing, behavioral patterns, sleep, eating, on-time arrival at work, sitting posture, reading posture, skin pigmentation patterns, moles, rushes, body temperature, and pulse rate.

26. The method of claim 24, further comprising a warning means for notifying medical centers and individuals about detected symptoms of illness and if requested, forwarding said collected information to said medical centers and individuals.

27. A computer program device readable by a machine, tangibly embodying a program of instructions executable by a machine to perform method steps for detecting an onset of illnesses and epidemics and preventing the illnesses and epidemics from occurring in individuals and a general population, said method comprising the steps of:

collecting information relating to health of individuals in a populated area via devices with sensors, said information being collected non-intrusively;

communicating said collected information for processing; and comparing collected information against a first database for determining if said collected information contains symptoms relating to said onset of illnesses, wherein diagnosis and prevention of the illnesses and epidemics in individuals is accomplished automatically without human intervention.

28. The computer program device of claim 27, wherein said devices with sensors are positioned at various fixed locations and with individuals.

29. The computer program device of claim 28, wherein said collected information is filtered.

30. The computer program device of claim 29, wherein a number of people in each segment of said collected information is counted.

31. The computer program device of claim 30, wherein said collection of information is initiated by an event selected from the group consisting of a receiving a signal from said processing means;

detecting of a number of people, in a vicinity of said devices with sensors, exceeding a certain threshold; and detecting of a preset condition by said devices with sensors.

32. The computer program device of claim 30, wherein said first database comprises symptoms, conditions and patterns of different illnesses.

33. The computer program device of claim 32, wherein said symptoms include appearance of tumors, colds, fever, indigestion, food poisoning, asthma, anemia, diabetes, shortness of breath.

34. The computer program device of claim 32, wherein said conditions include a higher than average body temperature, coughing, sneezing and nose blowing.

35. The computer program device of claim 32, further comprising the steps of:

receiving said collected information from said devices with sensors;

saving said collected information in a historical storage of said collected information; and comparing said collected information with information from said historical storage to determine if there is an increase of symptoms constituting an illness.

36. The computer program device of claim 35, further comprising a step of comparing said collected information with information from said database to determine what particular illness is represented by said increased symptoms determined by said first comparison means.

37. The computer program device of claim 36, further providing statistical analysis consisting of counting various factors, events and, sequences in said filtered information and estimating probabilities of said factors, events, and sequences.

38. The computer program device of claim 37, wherein said various factors, events and, sequences include coughing, nose blowing, sneezing, behavioral patterns, sleep, eating, on-time arrival at work, sitting posture, reading posture, skin pigmentation patterns, moles, rushes, body temperature, and pulse rate.

39. The computer program device of claim 37, further comprising a warning means for notifying medical centers and individuals about detected symptoms of illness and if requested, forwarding said collected information to said medical centers and individuals.

* * * * *